(12) United States Patent
Huiku et al.

(10) Patent No.: US 7,447,541 B2
(45) Date of Patent: Nov. 4, 2008

(54) MONITORING SUBCORTICAL RESPONSIVENESS OF A PATIENT

(75) Inventors: Matti Veli Huiku, Epsoo (FI); Iikka Kimmo Korhonen, Lempäälä (FI)

(73) Assignee: Instrumentarium Corporation, Helsinki (FI)

( * ) Notice: Subject to any disclaimer, the term of this patent is extended or adjusted under 35 U.S.C. 154(b) by 557 days.

(21) Appl. No.: 10/881,019

(22) Filed: Jun. 30, 2004

(65) Prior Publication Data
US 2006/0004296 A1  Jan. 5, 2006

(51) Int. Cl.
*A61B 5/04* (2006.01)
(52) U.S. Cl. .................. 600/544; 600/554; 600/485
(58) Field of Classification Search ............. 600/544, 600/557, 545, 485, 500, 481, 301, 513, 407
See application file for complete search history.

(56) References Cited

U.S. PATENT DOCUMENTS

| | | | | |
|---|---|---|---|---|
| 4,570,640 A * | 2/1986 | Barsa | ................... | 600/554 |
| 4,869,264 A | 9/1989 | Silberstein et al. | | |
| 5,439,900 A * | 8/1995 | Bukusoglu et al. | .......... | 514/170 |
| 5,775,330 A * | 7/1998 | Kangas et al. | ............... | 600/544 |
| 5,957,885 A * | 9/1999 | Bollish et al. | ................ | 604/67 |
| 6,016,444 A * | 1/2000 | John | ........................ | 600/544 |
| 6,032,072 A * | 2/2000 | Greenwald et al. | .......... | 600/544 |
| 6,120,443 A | 9/2000 | Cohen-Laroque | | |
| 6,161,044 A * | 12/2000 | Silverstone | ................. | 607/45 |
| 6,248,126 B1 * | 6/2001 | Lesser et al. | ............... | 607/113 |
| 6,317,627 B1 * | 11/2001 | Ennen et al. | ................ | 600/544 |
| 6,351,674 B2 * | 2/2002 | Silverstone | ................. | 607/46 |
| 6,526,297 B1 * | 2/2003 | Merilainen | .................. | 600/310 |
| 6,631,291 B2 * | 10/2003 | Viertio-Oja et al. | ......... | 600/544 |
| 6,745,764 B2 * | 6/2004 | Hickle | .................. | 128/203.12 |
| 6,757,558 B2 * | 6/2004 | Lange et al. | ................ | 600/544 |
| 6,768,920 B2 * | 7/2004 | Lange et al. | ................ | 600/545 |
| 6,826,426 B2 * | 11/2004 | Lange et al. | ................ | 600/544 |
| 6,934,579 B2 * | 8/2005 | Mantzaridis et al. | ........ | 600/544 |

(Continued)

FOREIGN PATENT DOCUMENTS

EP      0 553 162      5/1997

(Continued)

OTHER PUBLICATIONS

*Prediction of the haemodynamic response to tracheal intubation: comparison of laser-Doppler skin vasomotor reflect and pulse wave reflux*, M. Luginbuhi et al., British Journal of Anaesthesia 89 (3): 389-97 (2002).

(Continued)

*Primary Examiner*—Charles A. Marmor, II
*Assistant Examiner*—Anita Saidi
(74) *Attorney, Agent, or Firm*—Andrus, Sceales, Starke & Sawall, LLP (57) ABSTRACT

To monitor subcortical responsiveness of a patient at least one first measurement signal is acquired from a patient and at least one second measurement signal is derived from the at least one first measurement signal. The second measurement signal is indicative of pain-related activity in the patient. A predetermined stimulus signal is then supplied to the patient and a response caused by the stimulus signal in the at least one second measurement signal is monitored in synchronization with the supplying of the stimulus signal. Based on the monitoring step, an indicator of subcortical responsiveness is determined, the indicator being indicative of the patient's level of antinociception.

24 Claims, 2 Drawing Sheets

U.S. PATENT DOCUMENTS

| | | |
|---|---|---|
| 7,089,927 B2 * | 8/2006 | John et al. ............. 128/200.24 |
| 7,198,605 B2 * | 4/2007 | Donofrio et al. ............ 600/559 |
| 7,204,833 B1 * | 4/2007 | Osorio et al. ................ 606/22 |
| 7,209,787 B2 * | 4/2007 | DiLorenzo ................... 607/45 |
| 2002/0017296 A1 * | 2/2002 | Hickle ................... 128/203.12 |
| 2003/0055343 A1 * | 3/2003 | Korhonen ................... 600/481 |
| 2003/0145854 A1 * | 8/2003 | Hickle ................... 128/204.18 |
| 2005/0010116 A1 * | 1/2005 | Korhonen et al. ........... 600/481 |
| 2005/0143665 A1 * | 6/2005 | Huiku et al. ................ 600/500 |
| 2005/0182338 A1 * | 8/2005 | Huiku ........................ 600/544 |
| 2005/0272984 A1 * | 12/2005 | Huiku ........................ 600/301 |
| 2006/0217614 A1 * | 9/2006 | Takala et al. ................ 600/481 |
| 2006/0217615 A1 * | 9/2006 | Huiku et al. ................ 600/484 |
| 2007/0010723 A1 * | 1/2007 | Uutela et al. ................ 600/301 |
| 2007/0055114 A1 * | 3/2007 | Viertio-Oja et al. ......... 600/300 |

FOREIGN PATENT DOCUMENTS

| | | |
|---|---|---|
| EP | 1 273 265 | 1/2003 |
| EP | 1516581 | 3/2005 |
| EP | 1 563 789 | 8/2005 |
| WO | WO-01/74240 | 10/2001 |
| WO | WO-02/32305 | 4/2002 |

OTHER PUBLICATIONS

*Skin Vasomotor Reflecet Predicts Circulatory Response to Laryngoscopy and Intubation*, Shimoda et al., Anesthesiology: vol. 88(2), Feb. 1998, pp. 297-304.

Partial European Search Report dated Nov. 23, 2005.

\* cited by examiner

MONITORING SUBCORTICAL RESPONSIVENESS OF A PATIENT

FIELD OF THE INVENTION

The present invention relates generally to a method and apparatus for monitoring subcortical responsiveness of a patient.

BACKGROUND OF THE INVENTION

Pain is an unpleasant sensory or emotional experience that is associated with actual or potential tissue damaging stimuli. It is always an individual and subjective sensation, which may be acute (nociceptive), elicited by noxious stimuli, or chronic pain that has outlived its usefulness to preserve tissue integrity. The perception of pain takes mainly place at cortex, and it may be suppressed in deep sedation and anesthesia by the general (global) inhibitory effects of sedative drugs and anesthetic agents. The responses to noxious stimulus may also be suppressed when the pain signal pathway is sufficiently suppressed at the subcortical level, often in the region of the brainstem and spinal cord. Both cortical and subcortical mechanisms play a role in pain management in modern surgical anesthesia or intensive care.

Analgesia refers to the absence of pain or loss of sensitivity to pain without unconsciousness in response to stimulation that would normally be painful.

Noxious stimuli, such as pin pricks or inflammation exceeding a certain threshold stimulus level in nociceptive nerve fibers (nociceptors), cause a nociception, i.e. a neuronal signal or perception that denotes the induced pain or injury. Nociception is transmitted in the Central Nervous System (CNS) via several different ascending pathways causing responses that can be cortical pain responses or subcortical stress responses. NSAIDs (Non-Steroidal Anti-inflammatory Drugs) effectively relief pain at a damaged tissue site, whereas opioids selectively affect the pain pathways in the region of the spinal cord or the brainstem. The local anesthetic agents, for instance those used in epidural analgesia, block both the pain and the sensory pathways in the spinal cord region.

Antinociception normally refers to the blocking or suppression of nociception in the pain pathways at the subcortical level. It may be described as subcortical analgesia, in distinction to preventing the perception of pain at the cortex, i.e. cortical analgesia. In this context, nociception generally refers to conscious or unconscious perception of physiological pain, while antinociception generally refers to inhibition of such perception.

Sedation is a drug-induced state of a patient, during which the patient may respond normally to verbal commands or tactile stimulation and is not agitated or anxious (mild sedation), or during which the patient responds only to loud commands or tactile stimulation (moderate or conscious sedation), or during which the patient is unconscious and not easily arousable, but responds only to repeated or painful stimulation (deep or unconscious sedation). Anesthesia, in turn, is the deepest drug-induced state of sedation, during which the patient is not arousable, even by painful stimulation.

Agitation is often defined as the motor restlessness that accompanies anxiety. Mild or moderate sedation is induced to remove the agitation and to ensure optimal patient management. Optimal level of sedation varies with the stimulation affecting the patient and is often achieved, for ventilated patients, at the deepest sedation, accompanied with sufficient analgesia.

The autonomic nervous system (ANS) is the 'unconscious' nervous system, which controls and regulates virtually all of our basic body functions, such as cardiac function, blood circulation and glandural secretion. The main parts of the ANS are the parasympathetical and sympathetical nervous branches. The sympathetical nervous system usually prepares us for high stress situations by speeding up the body functions. Under conditions of normal ANS regulation, the parasympathetical system restores the normal conditions in blood circulation by slowing down the heart rate. Pain, discomfort, and surgical stress may activate the sympathetical branch of the ANS and cause an increase in blood pressure, heart rate and adrenal secretions.

Neuromonitoring is a subfield of clinical patient monitoring focused on measuring various aspects of brain function and on changes therein caused by drugs commonly used to induce and maintain anesthesia in an operation room or sedation in patients under critical or intensive care.

Electroencephalography (EEG) is a well-established method for assessing brain activity by recording and analyzing the weak biopotential signals generated in the cortex of the brain with electrodes attached on the skin of the skull surface. The EEG has been in wide use for decades in basic research of the neural systems of the brain, as well as in clinical diagnosis of various neurophysiological diseases and disorders.

Electromyography (EMG) is a method for recording electrical biopotentials of muscles. In an EMG measurement, the electrodes are attached on the surface of the skin at a muscle group. An EMG signal is often recorded from the skull of the patient, whereby the recorded signal indicates both the activity of the facial muscle (fEMG) and the brain (EEG). As the frequencies of the EMG spectrum are usually high and above the frequencies of brain activity, the signal components can be separated by methods of signal processing or spectral analysis from the EEG signal.

Electrocardiography (ECG) is another well-established method for assessing cardiac function by recording and analyzing the biopotential signals generated in the heart. Electrodes are attached on the skin of the chest with more peripheral references. The ECG is commonly used for diagnosing cardiac dysfunctions, various cardiac and circulatory diseases, and arrhythmias. Heart rate (HR), often derived from the ECG waveform, is one of the most important parameters characterizing the condition of a patient.

Respiration rate is another vital sign, which is often monitored even in basic patient care. In connection with anesthesia and sedation of ventilated patients, monitoring of the respiration is often combined with monitoring of gas exchange, which includes monitoring of inhaled and exhaled oxygen, carbon dioxide and anesthetic gases. In modern gas monitors, airway pressure (AWP) and gas flows are also measured in order to improve the safety and quality of the ventilation.

Blood pressure (maintaining blood circulation) is yet another vital sign obtained from a patient. It may be monitored either non-invasively (NIBP) or invasively (InvBP) using catheters inserted in the arteries or veins. The latter techniques are continuous and they allow a detailed monitoring of the regulation of the cardiac-circulatory and pulmonary functions.

Pulse oximetry is a well-established technique for measuring oxygen saturation (SpO2) in arterial blood. SpO2 is an important parameter, nowadays often called as the fourth vital sign, which relates to the adequacy of oxygen supply to peripheral tissues and organs. Pulse oximeters also display a photoplethysmographic (PPG) pulse waveform, which can be related to tissue blood volume and blood flow, i.e. the blood circulation, at the site of the measurement, typically in finger or ear.

Analysis methods using the heart rate variability (HRV) are emerging techniques for diagnosing cardiac diseases, such as lack of oxygen supply to the cardiac muscle, and for characterizing the cardiac function and the condition of the patient in general. Fast changes in the heart rate are usually caused by the parasympathetical ANS control mediated in the vagal cranial nerve. Vagal control slows down the heart beat. The slow variations (<0.15 Hz) of the heart rate are mainly associated with sympathetical activity, which accelerates the heart beat. The ratio of the fast components of the HRV to the slow components of the HRV is often called the sympatho-vagal balance.

One of the special applications to which a significant amount of attention has been devoted during the past few years is the use of processed EEG signals for objective quantification of the brain function for the purpose of determining the level of consciousness. Here, the basic idea is to automatically detect if the subject or patient is unconscious or conscious. Specifically, this has become an issue, both scientifically and commercially, in the context of measuring the depth of anesthesia during surgery. The concept of the adequacy of anesthesia, which is a broader concept, further includes various other aspects relating to the quality of anesthesia, such as the state of the autonomic nervous system (ANS), and more specifically analgesia, i.e. loss of sensation of pain.

The assessment, measurement, or control of the different components of anesthesia or sedation is difficult and sometimes poorly defined, as the drugs used are often unspecific and influence many components simultaneously. The cortical components, i.e. hypnosis, amnesia (loss of memory) and perception (i.e. experience) of pain and conscious control of movements, mainly refer to the activity of the cortex and integrity of the cortical evaluations of the sensory afferent inputs and the ability to store information and control the body. Loss of consciousness, i.e. loosing responses to non-noxious sensory stimulations, such as spoken commands, is dominantly related to the overall suppression of cortical processing and awareness, which already in an early phase of light sedation lead to the loss of explicit memory. Therefore, the monitoring of the loss of consciousness and/or awareness is usually enough to guarantee an adequate amnesia of the patient, as well.

During the past few years, several commercial devices for measuring the level of consciousness and/or awareness in a clinical set-up during anesthesia have become available. These devices, which are based on a processed one-channel EEG signal, have been introduced e.g. by Aspect Medical (Bispectral Index), by Datex-Ohmeda (Entropy Index) and by Danmeter (an auditory evoked EEG potential monitoring device, AAI™). At present, the situation with the assessment of the cortical activity and integrity is considered satisfactory, though not resolved for all applications.

As to the central nervous system (CNS), the assessment or measurement of the suppression of the subcortical activity, the ANS and the integrity of subcortical evaluations is far more unsatisfactory. No commercial devices exist for this purpose. This is mainly because the sub-cortical components are not represented in any single bioelectrical or other signal, in contrast to that the EEG almost alone may represent the cortical activity. The monitoring of the adequacy of anesthesia or sedation thus—in addition to monitoring the hypnotic state of brains by EEG—call for a multi-parameter approach, which combine parameters describing the overall responsiveness of the patient to "unconscious" stimulations. This may be defined by means of the hemodynamic, motor, and endocrine stability. A promising basis for searching a multi-parameter monitoring method for sub-cortical activity can thus possibly be found from the subtle features in the common vital signs, the heart rate, the respiration rate, the blood circulation, and the blood pressure.

The sub-cortical integrity of the afferent input, ANS evaluations, and efferent output is best researched with noxious stimulations and their responses, as these are mainly processed and modulated in the brainstem and spinal levels. The responses can also be modulated (attenuated) by analgesic or antinociceptive drugs, which influence the pain pathways at the sub-cortical levels. A successive monitoring method shall thus demonstrate a clear relationship and correlation between both the effect (concentration) of the analgesics on the suppression of the noxious event responses and the intensity of the noxious stimulations on the strength or amount of the responses in the parameters.

The need for reliable monitoring of the adequacy of anesthesia is based on the quality of patient care and on economy related aspects. Balanced anesthesia reduces surgical stress, and there is also evidence that adequate analgesia decreases postoperative morbidity. Awareness during surgery with insufficient analgesia may lead to a post-traumatic stress disorder. Prolonged surgical stress sensitizes the central pain pathways, which post-operatively increases patient pain and secretion of stress hormones. Low quality pre- and intra-operative analgesia makes it difficult to select the optimal pain management strategy later on. More specifically, it may cause exposure to unwanted side effects during the recovery from the surgery. Too light an anesthesia with insufficient hypnosis causes traumatic experiences both for the patient and for the anesthesia personnel. From economical point of view, too deep an anesthesia may cause increased perioperative costs through extra use of drugs and time, and also extended time required for post-operative care. Too deep a sedation may also cause complications and prolong the usage time of expensive facilities, such as the intensive care theater.

International patent application WO 02/32305 discloses a method and device for ascertaining the cerebral state of a patient. In this disclosure, a measure derived from EMG signal data enhances and confirms the determination of the hypnotic state made using EEG signal data. As the EMG data may be computed more frequently than the EEG data, this renders ascertaining changes in the hypnotic state of the patient more rapid. In this method, the (facial) EMG thus alone reflects the suppression of the nociceptive pathways. State entropy (SE), which is calculated in the low frequency band up to 32 Hz, is dominated by the cortical EEG activity, while response entropy (RE), which also includes the high frequencies, represents both the cortical and muscle activity. The difference RE-SE is, therefore, a measure of the (f) EMG power, which will increase at nociception and which, therefore, may be a good measure of the suppression of the pain pathways. However, the above-mentioned dependency on the medication of the patient may render the method unusable in certain situations. As the (facial) electromyography signal is affected by neuro-muscular blocking agents (NMBAs), which suppress signaling at the nerve-muscle junctions, the EMG component of the measurement may vanish and render the method unusable, if the medication of the patient includes neuro-muscular blocking agents. It shall also be emphasized that the difference RE-SE is not specific to the suppression of the pain pathways but also reflects the overall motoric activity following any arousals—that is emotional or normal sensory evoked arousals, too. For instance, when the patient is awake and not perceiving any pain or discomfort, the RE-SE difference is typically about 8-10 percent. At deep hypnosis painful stimulations can cause RE to differ from SE, but it is difficult to tell at which level the transition to the only-nociception induced varying difference takes place.

EP Patent 0553162 proposes a method and apparatus for assessing the depth of anesthesia by using respiratory sinus arrhythmia (RSA) as a measure of the state of the brain. The document describes a method in which a parameter indicative of clustering of the heart beat pattern is determined from the ECG waveform relative to the beginning of each respiration cycle. This parameter is then compared with a reference value calculated using a test for randomness. The parameter is then compared with the reference value to derive a measurement of the depth of anesthesia. In particular with spontaneously breathing anesthetized patients, the clustering is proportional to the RSA, which decreases with deepening anesthesia. The heart rate changes influencing the clustering are primarily controlled by the parasympathetical branch of the ANS, and therefore, the depth of anesthesia is related to the parasympathetical activity. This, however, correlates poorly with sympathetical effects, i.e. with the pain and nociception, and therefore also poorly with the adequacy of analgesia. Furthermore, the clustering takes place differently in artificial overpressure ventilation and in spontaneously breathing patients, as the heart rate always accelerates during the low pressure period of the respiration cycle and decelerates during the high pressure phase. The proposed method works reasonably well for spontaneously breathing patients, who in addition have a large RSA, such as children, but often fails in connection with artificially ventilated older patients. Pain reduces RSA amplitudes, as does the deepening of anesthesia. Hence, this approach does not provide a separation between the hypnotic and analgesic components of anesthesia or sedation.

U.S. Pat. No. 6,120,443 also suggests a method based on a heart beat interval (ECG R-to-R peak interval, RRI) analysis to assess the depth of anesthesia. In this method, the degree of randomness of the heart beats is described by means of a fractal dimension of the series of the R-R Intervals, mathematically describing the correlation within the RRI series. High correlation is indicative of a low fractal dimension and of only very few (CNS) processes, which add irregularities in the RRI series. Low correlation and thus high randomness equals high fractal dimension, which implies that the anesthesia is light and that many processes influence the RRI series. The methods for calculating the fractal dimensions are computationally heavy. In addition, the suggested method suffers from the fact that the degree of both hypnosis and analgesia affect the fractal dimension. The orthogonality of the two measures corresponding to the cortical and subcortical activity is thus poor. Although the method was primarily suggested for measuring the hypnosis of the patient, it is probable that it will also correlate with the degree of the surgical stress, which increases hemodynamic instabilities and the fractal dimension of the RRI series. Using this method, it is thus difficult to tell, whether the anesthetist should add or reduce opioids or hypnotic drugs.

European patent application EP1273265 describes a simpler method for analyzing an RRI and a blood pressure (BP) time series. Furthermore, the method tries to make a clear distinction between the sympathetical and parasympathetical cardiovascular responses. The sympathetical responses correlating with the surgical stress increase the heart rate and blood pressure. The acceleration index of the heart rate and the index for the increase of the blood pressure is calculated using a filter, a kind of edge filter, which detects the increasing slopes in the values of RRI or BP, but neglects the decreasing values. The document suggests that these indices may be used as a measure of the adequacy of analgesia. However, the method lacks the specificity to noxious stimuli and detects also the variations caused by respiration and other increasing slopes resulting from normal sympathetical activation without noxious stimulation.

The prior art technologies thus aim to describe the adequacy of anesthesia using a unidimensional concept for the depth of anesthesia. They do not account for separate hypnotic and analgesic components, which are orthogonal, i.e. as much independent of each other as possible, and specific to the hypnotic and analgesic medications given during anesthesia. Thus the prior art methods cannot answer the question, whether one should add or reduce the analgesics or hypnotics in order to restore a balanced anesthesia. All prior art technologies that are claimed to measure the adequacy of analgesia show a considerable dependence on the level of hypnosis and, consequently, at light anesthesia without any noxious stimulations show a value that is usually associated with poor analgesia. Furthermore, prior art mechanisms do not allow accurate pain management in anticipation of certain treatment, such as surgery.

The present invention seeks to alleviate or eliminate the above drawbacks associated with the above-described measurements and to bring about a mechanism that allows monitoring and evaluation of the analgesic component required for accomplishing optimal pain management during the treatment of a patient, especially during a surgery.

SUMMARY OF THE INVENTION

The present invention seeks to provide a mechanism for monitoring the subcortical responsiveness of a patient. Depending on whether the state of the patient is examined with regard to transmission or suppression of nociception in the pain pathways, the subcortical responsiveness may, respectively, be indicative of the level of nociception or antinociception of the patient. Below, the level of antinociception is used as a common term that covers both alternatives.

The invention further seeks to provide a mechanism that allows the analgesic component of anesthesia or sedation to be evaluated accurately in order to optimize pain management during the treatment of a patient, especially when the patient is under anesthesia or sedation.

In the present invention, first and second measurement signals are obtained from the patient. The first measurement signal may be a physiological signal measured from the patient, such as a heart rate signal, but it may also be a signal representing a variable refined from one or more physiological signals measured from the patient. The second measurement signal, in turn, is a signal derived from the first measurement signal, and it is indicative of pain-related activity in the patient. Although pain-related activities in the patient may relate to increased motoric activity, they most often relate to the activation of the sympathetical branch of the autonomic nervous system. A predetermined stimulus signal is then supplied to the patient and the second measurement signal is monitored in synchronization with the stimulus signal to detect the response caused by the stimulus signal in the second measurement signal. Based on the response detected, a parameter is calculated, which is here termed the indicator of subcortical responsiveness. As discussed above, this indicator is indicative of the level of nociception or antinociception of the patient, i.e. it indicates the level of transmission or suppression of nociception in the pain pathways.

Several first measurement signals of different types may also be utilized, in which case several second measurement signals may also be obtained. In this case, the indicator of subcortical responsiveness is calculated based on the responses detected in more than one second measurement signal.

Thus one aspect of the invention is providing a method for monitoring subcortical responsiveness of a patient. The method includes the steps of acquiring at least one first measurement signal from a patient and deriving at least one second measurement signal from the at least one first measurement signal, each second measurement signal being indicative of pain-related activity in the patient. The method further includes the steps of supplying a predetermined stimulus signal to the patient, monitoring a response caused by the stimulus signal in the at least one second measurement signal, wherein the monitoring step is synchronized with the supplying step, and determining, based on the monitoring step, an indicator of subcortical responsiveness, said indicator being indicative of the patient's level of antinociception.

Another aspect of the invention is that of providing an apparatus for monitoring the level of nociception of a patient. The apparatus includes first means for acquiring at least one first measurement signal from a patient and second means for deriving at least one second measurement signal from the at least one first measurement signal, each second measurement signal being indicative of pain-related activity in the patient. The apparatus further includes stimulator means for supplying a predetermined stimulus signal to the patient, third means for monitoring a response caused by the stimulus signal in the at least one second measurement signal, the monitoring means being synchronized with the stimulator means, and fourth means, responsive to the third means, for determining an indicator of subcortical responsiveness, said indicator being indicative of the patient's level of antinociception.

The invention provides a mechanism for improved pain management during the treatment of a patient. In particular, the invention provides an improved mechanism for managing surgical or therapeutical pain. Since the mechanism allows the state of the patient to be compared against a fixed scale of nociception/antinociception, the effect of an analgesic on a particular patient may be evaluated and "tuned" before the surgery or therapeutic action is started. The patient's level of antinociception may thus be evaluated and controlled in respect of an upcoming pain to be imposed on the patient. Therefore, the amount of an analgesic corresponding to the surgical pain to be imposed on the patient may be determined in advance, without having to find out the optimum level of analgesia during the actual surgery. In other words, the supply of analgetics may be adapted to the upcoming pain prior to the actual treatment causing pain Thus, the well-being of the patient during a surgery or intensive care may be improved, since the amount of surgical or therapeutic pain, and also the periods of surgical pain, may be diminished due to the fact that the supply of an analgesic may be adapted to an upcoming treatment with improved accuracy prior to the actual treatment.

Other features and advantages of the invention will become apparent by reference to the following detailed description and accompanying drawings.

BRIEF DESCRIPTION OF THE DRAWINGS

In the following, the invention and its preferred embodiments are described more closely with reference to the examples shown in FIG. 1 to 4 in the appended drawings, wherein.

DETAILED DESCRIPTION OF THE INVENTION

Figure 1:
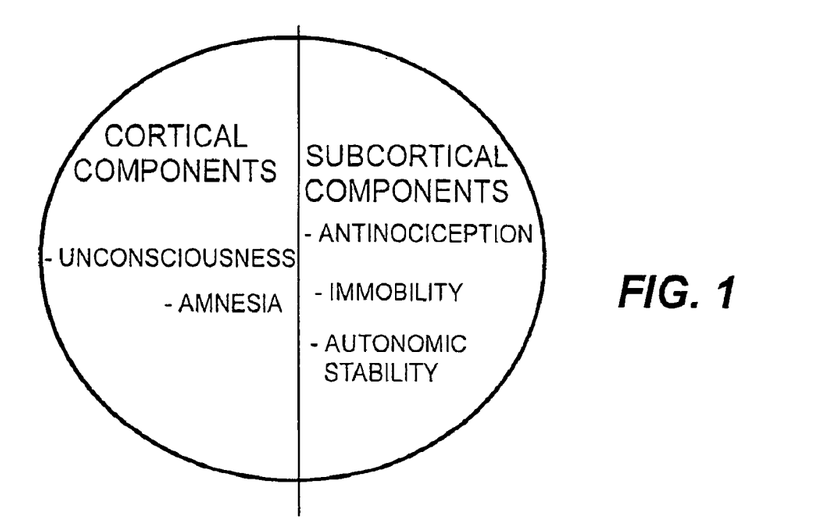
FIG. 1 illustrates the concept of the quality of anesthesia.

FIG. 1 illustrates the concept of the quality of anesthesia. According to the current comprehension, the quality of anesthesia includes five different components: hypnosis (i.e. unconsciousness), amnesia, antinociception, immobility, and the stability of the ANS. The first two components, the hypnosis and amnesia, are of cortical origin and are indicative of cortical activities. The suppression of the cortical activity is obtained by drugs, which typically effect neural signaling globally in the brain. The drugs may activate the natural inhibitory GABA (gamma-aminobutyric acid) receptor system in the brains or prevent, by an unknown mechanism, neural signaling in the synapses between the neurons. For this reason, the drugs often also affect other parts than the cortex in the brain, thereby also suppressing subcortical activity.

The other components in the anesthesia model, which are indicative of sub-cortex related activity in the patient, are much more specific and often relate to altering, modulating or disturbing neural signaling at certain receptor or neurotransmitter level. These components can be affected selectively by different specific drugs. For instance, antinociception, i.e. the suppression of the neural transmission in the pain pathways, is achieved by opioid drugs, which affect the opioid/enkephalin receptors and activate the descending pathways, which block or modulate the nociceptive stimuli in the spinal cord. Furthermore, the NMBA drugs block the neural transmission in peripheral neuro-muscular junctions, which results in one kind of specific immobility of a patient. The stability of the ANS and the antinociception are closely related, since noxious stimulation in deep anesthesia causes hemodynamic and hormonal instability. The stability of the ANS is therefore also advanced by opioid drugs and by several other drugs, which may affect specifically the parasympathetical or sympathetical activities of the ANS.

Although many drugs may be involved in achieving an adequate level of the cortical and subcortical activity, the adequacy of anesthesia is often managed only by a gas anesthetic agent or other hypnotic agent, which dominantly (and globally) affects the cortical activity, and by an opioid, which selectively modulates the pain pathways at subcortical level, and by a NMBA drug, which induces immobility in peripheral nerve-muscle junctions. The effects of the hypnotic agent may be monitored, for instance, by the above-described methods based on calculation of spectral entropy and the neuromuscular blockade by an NMT (NeuroMuscular Transmission) measurement. The hypnotic and NMBA drugs can then be administered based on these measurements. The present invention provides a mechanism for evaluating the patient's current level of antinociception in view of an upcoming pain and for adapting the supply of analgetics to the upcoming pain prior to the actual treatment causing pain.

Figure 2:
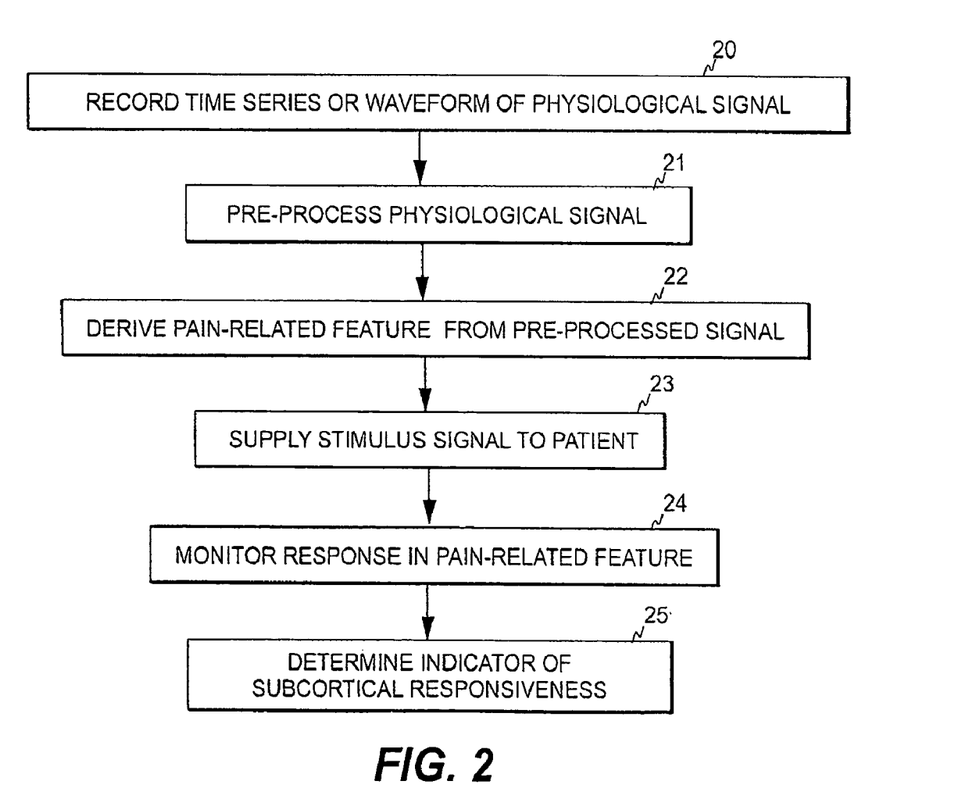
FIG. 2 is a flow diagram illustrating one embodiment of the invention.

FIG. 2 illustrates one embodiment of the present invention. For the actual measurement, signal data is first obtained from the patient (step 20). This may be implemented in a conventional manner, i.e. while the patient is connected to the patient monitoring system, a physiological signal is recorded and stored in a memory of a monitoring device. The physiological signal may be, for example, an ECG waveform or a photoplethysmographic, a blood pressure or a respiration waveform, or a signal representing a physiological trend parameter, such as heart rate, pulse rate, systolic, diastolic or mean blood pressure. The physiological signal may also be an fEMG signal or a skin conductivity signal. Typically, waveforms are sampled at about 100 samples/sec, and the trend parameters effectively at a rate of about 10 samples in a minute.

The recorded signal data may then be pre-processed at step 21 for extracting the parameters that are not directly available as a trend parameter, such as beat-to-beat or cycle-to-cycle intervals of the waveform. For example, to obtain an RRI signal the moments at which the R-peaks occur in the QRS-complex are extracted from an ECG waveform, and the R-to-R intervals are recorded. In case of a plethysmographic waveform, the pulse amplitude may be extracted for each pulse beat.

A time series is then formed from Lhe values of the extracted signal. It may sometimes be advantageous to examine the changes of the signal instead of the absolute values, such as amplitudes or intervals. Therefore, the time series of the physiological parameter may be pre-processed by derivation of the signal in order to enhance fast changes and responses. This is especially important in the analysis of plethysmographic amplitudes, in which slow changes may be associated with fluid balance, change of attitude or temperature, or with slow hormonal control of the body. The pre-processing phase, i.e. step 21, may also include filtering out some of the frequency components of the signal or rejecting artifacts, as well as correcting or removing some of the values of the signal, such as ectopic beats of the ECG wave.

From the pre-processing phase, a sequence of signal values representing a physiological signal or parameter is thus obtained. In the following this sequence is also termed the first measurement signal. It is assumed in the embodiment of FIG. 2 that a single physiological signal is measured from the patient. However, several physiological signals may also be measured simultaneously from the patient, in which case several first measurement signals may also be obtained.

In the next step of the embodiment of FIG. 2, a pain-related feature is derived from the first measurement signal (step 22). Although in case of an fEMG signal the pain-related feature is the power of the EMG signal, the pain-related feature relates most often to the activation of the sympathetical branch of the autonomic nervous system. A pain-related feature indicative of activity in the ANS of the patient is in this context also termed an ANS component. The ANS component thus refers to a pain-related feature which is indicative of the status of the ANS of the patient, i.e. of activity in the sympathetical and/or parasympathetical branch of the ANS. The sympathetical and parasympathetical activations appear in various signals in a characteristic way depending on the signal in question, but in opposite manners: sympathetical activation accelerates the heart rate, increases blood pressure, and constricts the blood vessels, for example, while the parasympathetical responses show up in the opposite manner, especially in the heart rate. The sympathetical responses occur with a delay of a few seconds, while the parasympathetical responses may appear more or less immediately and are alone responsible for all variations, which have the frequency range higher than about 0.15 Hz. The sympathetical branch of the ANS may activate variations with periods longer than about 10 sec. These low frequency components of the variability of the physiological signal or parameter are thus dominantly associated with sympathetical regulation. A typical noxious response pattern in a physiological parameter is such that after the stimulus a parasympathetical withdrawal takes place, after which the sympathetical activation takes over, and the change in the signal continues in the same direction. Therefore, a noxious response may include initial fast components due to the switching off and on of the parasympathetical branch of the ANS. This, when repeated, leads to beat-to-beat irregularities in the cardiac-related physiological signal, or it may include a slow trend, like a change in the absolute level of the parameter value itself.

Very low frequency variations can usually be associated with hormonal regulation of the physiological parameter, with temperature regulation or with normal day-night rhythm or mood, or with activity changes in the person. These very low frequency components are actually harmful when noxious events are to be recognized and counted, and they can be filtered out in the pre-processing phase of the method.

Table 1 lists some of the most useful pain-related features which relate to various physiological signals and which may thus be used as an indication of the patient's level of antinociception. Apart from the EMG signal all pain-related features in the table are indicative of activity in the sympathetical branch of the ANS.

| Physiological Signal | Pain-related feature |
|---|---|
| Heart Rate (HR) | HR acceleration |
| HR | Low Frequency (LF) variability: LF spectral power, LF Standard Deviation (SD2 in Poincare analysis) |
| HR | The ratio of the LF variability to the High Frequency (HF) variability, so called sympatho-vagal ratio. |
| Blood Pressure (BP) | Elevated BP |
| BP | Low Frequency (LF) variability |
| BP | The ratio of the LF variability to the High Frequency (HF) variability, so called sympatho-vagal ratio. |
| Plethysmographic Amplitude (Pty_A) | Small and decreasing amplitude |
| Pty_A | LF variability |
| Pty_A | The ratio of the LF variability to the HF variability, so called sympatho-vagal ratio. |
| Pty_A | Beat-to-beat variability (Pty_B2B) excluding respiration variability |
| Pty_A | The ratio of Pty_B2B to the regular respiration variability (Pty_HF_Resp) (Pty_B2B/Pty_HF_Resp) |
| fEMG | fEMG power increase |
| RE | Change in EEG response entropy, or especially increase in RE − SE difference |
| SC, Skin Conductivity | Activation of the sweat glands, increase in the SC |

At step 22 in the embodiment of FIG. 2, a pain-related feature is thus derived from the pre-processed signal. The derived signal is in this context termed the second measurement signal.

The implementation may vary depending on the actual physiological signal. As can be seen from the above table, in case of an RRI time series, for example, the derived feature may be the low frequency variability in the inter-beat intervals of the RRI time series, which may be extracted by low-pass filtering the pre-processed signal. In case of a plethysmographic waveform for example, the ANS component may be derived as the irregularity of the beat-to-beat amplitude variability. However, the low frequency component of the variability of the inter-beat intervals may also be utilized as the sympathetical feature in connection with the plethysmographic waveform.

The pain-related feature may also be derived by combining at least some of the physiological signals in the pre-processing phase to produce a new signal serving as a second measurement signal. For example, a pain index signal indicative of the patient's level of antinociception may be calculated based on one or more of the physiological signals already in the pre-processing phase. The pain index signal may be calculated, for example, based on one or more physiological signals in the set including an RRI signal, a plethysmographic signal, and an EMG signal. The embodiment utilizing the pain index signal is thus otherwise the same as the embodiments discussed above, but the pain-related feature is derived by calculating index values based on different types of physiological signals. The pain index signal may be calculated, for example, as follows:

$$P(t) = \frac{1}{1 + \theta^{-(aX(t)+bY(t)+cZ(t)+d)}}$$

where

X(t), Y(t), and Z(t) represent the different physiological signals obtained from the patient, and a, b, c, and d are parameters selected to optimize the performance of the pain index signal.

In the above formula, the signal values X(t), Y(t), and Z(t) representing the different physiological signals are typically normalized values obtained, for example, by dividing the current value by the mean value of the parameter in question. As mentioned above, X(t), Y(t), and Z(t) may be based on RRI, plethysmographic, and EMG signals, for example.

In the next step of the method (step 23), a stimulus signal having predefined characteristics is applied to the patient. The stimulus signal may assume any form that allows an appropriate noxious or non-noxious signal to be supplied to the patient. The stimulus signal may therefore be an electrical, a mechanical, a chemical, or an auditory signal, for example. Moreover, the stimulus signal is predetermined in the sense that the monitoring system knows the parameters, such as the amplitude and pulse length, defining the stimulus signal.

The response caused by the stimulus signal in the second measurement signal is then detected, and based on the response detected an indicator of subcortical responsiveness is determined for the patient (steps 24 and 25). The indicator may be calculated in various ways. For the determination of the indicator the response is typically compared with the second measurement signal obtained without a stimulus signal in order to evaluate the (relative or absolute) change caused by the stimulus signal in the second measurement signal. Therefore, the difference between the two situations (presence and absence of the stimulus signal) is typically evaluated, although the ratio of the signal values of the two situations may also be calculated. Furthermore, the indicator of subcortical responsiveness may further be normalized to a fixed range, such as between 0 and 100.

In the embodiments in which several second measurement signals, derived from several first measurement signals, are utilized, the change caused by the stimulus signal may be evaluated separately for each of the second measurement signals. The final indicator of subcortical responsiveness may then be calculated based on the individual indicators obtained from each of the second measurement signals. In the calculation of the final indicator, the individual indicators may be given different weights.

In the present invention, the ANS of the patient is thus treated as a "black box" studied on a stimulus-response basis by supplying a well-defined stimulus signal and monitoring the response in synchronization with the supplying of the stimulus signal. The responses are detected and discriminated from spontaneous ANS activity by means of phase information that allows the effect of the stimulus to be detected in the second measurement signal.

In one embodiment of the invention, the monitoring system allows the parameters defining the stimulus signal to be controlled by the nursing staff. Different treatment types, causing different levels of nociception, may be mapped to different stimulus signals, whereby each mapped pair corresponds to a certain level of nociception.

Although the stimulus signal may be a single pulse supplied to the patient, in one embodiment of the invention the stimulus signal is supplied to the patient repeatedly. The stimulus signal may thus consist of a sequence of stimulus pulses. The pulses in the sequence may be equal to each other or their characteristics may vary within the sequence. For example, the pulses may have an ascending (or descending) amplitude. The same applies to the interval between two consecutive pulses, i.e. the said interval may be fixed or it may vary within the sequence.

Figure 3:
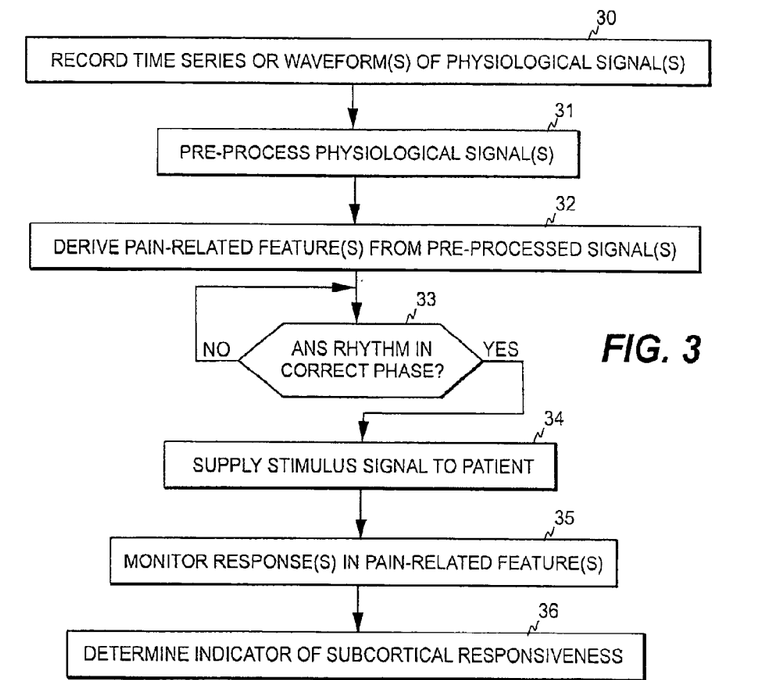
FIG. 3 is a flow diagram illustrating another embodiment of the invention.

In a further embodiment of the invention, the supplying of the stimulus signal is synchronized with a spontaneous rhythm regulated by the ANS, such as the respiration/ventilation rhythm of the patient. In other words, the stimulus signal is supplied at a certain phase of the rhythm. In this embodiment, which is illustrated in FIG. 3, the desired ANS rhythm is thus monitored and the stimulus signal is supplied when the ANS rhythm is in correct phase, as shown in step 33. As discussed below in connection with FIG. 4, the phase information of the ANS rhythm may be obtained in various ways.

Figure 4:
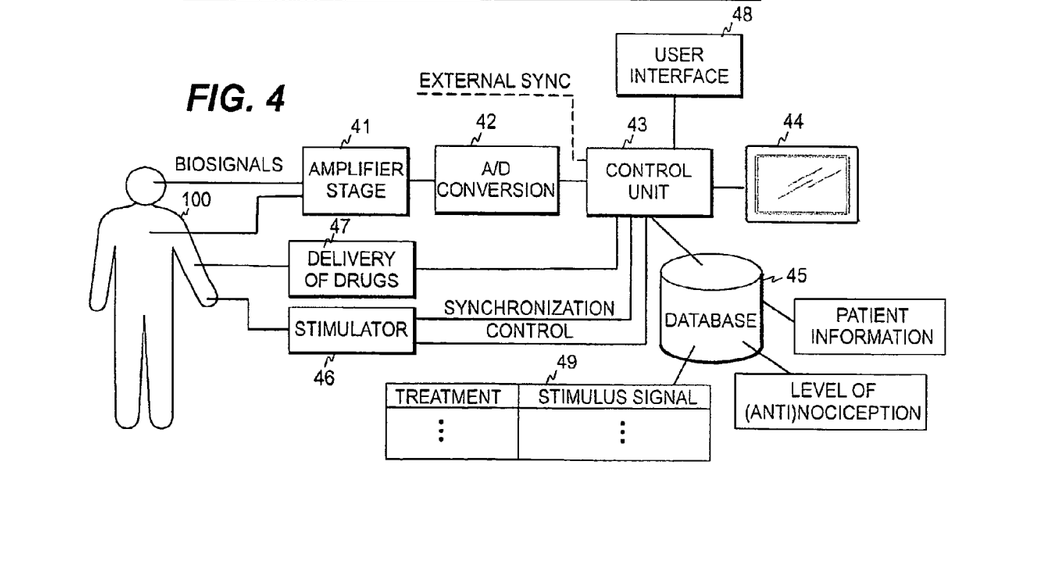
FIG. 4 illustrates one embodiment of a system according to the invention.

FIG. 4 illustrates one embodiment of the system according to the invention. The biosignals obtained from one or more sensors attached to a patient 100 are supplied to an amplifier stage 41, which amplifies the signals before they are sampled and converted into digitized format in an A/D converter 42. The digitized signals are supplied to a control unit 43 (including a microprocessor), which may then record the signals.

The control unit is provided with a database or memory unit 45 holding the digitized signal data obtained from the sensor(s). Using the data, the control unit may perform the above-described pre-processing phase and form the time series forming the first measurement signal. In connection with the pre-processing phase, the control unit may also retrieve patient information from the memory unit to check whether some of the physiological signals are to be omitted or given less weight when forming the first measurement signal. The memory unit may further include the information mapping different treatment types to different stimulus signals. In the example of FIG. 4, this information is in the form of a table 49.

In the embodiment of FIG. 4, the control unit also derives the second measurement signal (pain-related feature) from the first measurement signal by means of digital signal processing. The control unit further controls the timing of the measurement. For this purpose, the control unit may utilize, if the measurement is phase-locked to another ANS rhythm of the patient, phase information indicating the phase of said another ANS rhythm. The control unit may derive the said phase information from one or more of the biosignals obtained from the patient, or it may receive the phase information as an external synchronization signal from an external device, such as a respirator. This is illustrated by a dashed line in the figure. Using the phase information obtained, the control unit supplies a synchronization signal to a stimulator 46, which in turn supplies the stimulus signal, in synchronization with the ANS rhythm, to the patient. The control unit further determines the effect of the stimulus signal in the second measurement signal and calculates the indicator of subcortical responsiveness.

Although one control unit (processor) may perform the calculations needed, the processing of the data may also be distributed among different processors (servers) within a network, such as a hospital LAN (local area network).

The control unit may display the results on the screen of a monitor 44 connected to the control unit, and it may further supply the calculated indicator as input data to a device or system 47 delivering drugs (analgetics) to the patient, which enables automatic control of the patient's level of antinociception. The system further includes user interface means 48 through which the user may control the operation of the system, such as the stimulus signal to be used.

In the following two different implementations of the invention are described, which rely, respectively, on an NMT module and on a TENS (Transcutaneous Electric Nerve Stimulation) device for supplying the stimulus signal to the patient.

In the first implementation, an NMT module is used for electrically stimulating the ulnar afferent nerve, for example. The stimulation current may be adjusted for obtaining an optimum response and known stimulation patterns, such as ST (Single Twitch) or TOF (Train of Four), may be used. The interval between successive stimulation pulses may vary from 3 to 30 sec, for example. The response in the heart rate, plethysmographic amplitude and/or pulse morphology, and/or blood pressure may be monitored synchronously with the stimulation. Several responses may be averaged and the averaged response may be used to determine the indicator of subcortical responsiveness. The main advantage of this embodiment is that it relies on an apparatus that is routinely available in operating rooms.

In the second embodiment, repeated small-scale noxious or non-noxious pulses are supplied to the patient and the ANS responses are continuously quantized. This stimulation mode is based on the observation that even single and small-scale noxious stimulus usually modulates normal ANS regulation rhythms, such as RSA (Respiratory Sinus Arrhythmia). In fact, even non-noxious stimulation, such as auditory stimulation, may cause this effect. However, the modulation is difficult to detect due to the complexity of the spontaneous ANS rhythms. If the supplying of the stimulus is synchronized with a spontaneous ANS rhythm, such as Mayer waves or the RSA, and if a repeating stimulus signal is used, it is possible to detect the modulation from the normal pattern of the ANS rhythm. When the stimulus is sufficiently small-scale, it is also ethically possible to apply the stimulation over extended periods of time without compromising patient safety.

In this stimulation mode, the stimulus signal, such as electric current, may be supplied synchronized with the ventilation or breathing rhythm of the patient and the change in the second measurement signal may be detected recording the values of the second measurement signal in the presence of the stimulation and in the absence of the stimulation. The stimulation pattern may therefore continuously vary between the said two states, i.e. the presence and absence of the stimulation. Two examples of such stimulation patterns are:

1-1-0-0-1-1-0-0, . . . , and
1-0-1-0-1-0-1-0, . . .

where "1" refers to supply of a stimulus during the ventilation/breathing cycle and "0" refers to omission of a stimulus during the ventilation/breathing cycle. The change in the second measurement signal may be detected by calculating the difference between the values of the second measurement signal obtained during the presence of the stimulation and during the absence of the stimulation. The main advantages of this approach are its potentiality for longer-term assessment of analgesia and improved specificity to nociception of changes in ANS related parameters.

The steps needed to derive the second measurement signal from the corresponding first measurement signal may vary depending on the physiological signal utilized. Sometimes, such as in case of an EMG signal, there may be only a slight difference between the two measurement signals. For example, the two measurement signals may be separated by an ordinary signal processing phase only, such as artifact rejection.

Although the invention was described above with reference to the examples shown in the appended drawings, it is obvious that the invention is not limited to these, but may be modified by those skilled in the art without departing from the scope and spirit of the invention.

The invention claimed is:

1. A method for monitoring subcortical responsiveness of a patient, the method comprising the steps of:
   acquiring at least one first physiological measurement signal from a patient using at least one sensor, the physiological measurement signal being one of the signals in a group including an RRI signal, a plethysmographic signal, an EMG signal, a blood pressure signal, and a signal representing skin conductivity;
   deriving at least one second measurement signal from the at least one first measurement signal, said at least one second measurement signal being indicative of pain-related activity in the patient;
   supplying a predetermined stimulus signal to the patient to cause pain to the patient, wherein the predetermined stimulus signal is supplied in synchronization with a spontaneous rhythm of the patient that is regulated by the autonomous nervous system of the patient;
   monitoring a response caused by the stimulus signal in the at least one second measurement signal, wherein the monitoring step is synchronized with the supplying step;
   determining, based on the monitoring step, an indicator of subcortical responsiveness, said indicator being indicative of the patient's level of antinociception; and
   outputting the indicator of subcortical responsiveness to a device.

2. A method according to claim 1, further comprising a step of synchronizing the supplying step with at least one of the at least one second measurement signal.

3. A method according to claim 1, wherein the supplying step is synchronized with an external synchronization signal.

4. A method according to claim 1, wherein the supplying step includes supplying a stimulus signal comprising a sequence of stimuli to the patient.

5. A method according to claim 4, wherein
the monitoring step includes detecting changes caused by each of said stimuli in the at least one second measurement signal; and
the determining step includes defining the indicator of subcortical responsiveness based on the changes detected.

6. A method according to claim 1, wherein the spontaneous rhythm of the patient is the respiration rhythm of the patient, wherein the synchronizing step includes synchronizing the supplying step with the respiration rhythm of the patient.

7. A method according to claim 1, wherein the acquiring step includes acquiring a single first physiological measurement signal from the patient, whereby a single second measurement signal is obtained in the deriving step.

8. A method according to claim 1, wherein the acquiring step includes a step of measuring a set of physiological signals from the patient.

9. A method according to claim 8, wherein the acquiring step further includes calculating the first physiological measurement signal based on the set of physiological signals.

10. A method according to claim 1, wherein
the acquiring steps includes a step of measuring a plurality of first physiological measurement signals from the patient; and
the deriving step includes the steps of normalizing each of the plurality of first physiological measurement signals and calculating the at least one second measurement signal based on the plurality of normalized physiological signals.

11. A method according to claim 10, wherein the calculating step includes calculating an index signal based upon the normalized first physiological measurement signals, wherein the index signal includes an independent, defined scale indicative of pain experienced by the patient.

12. A method according to claim 1, wherein the deriving step includes filtering at least one of the at least one first measurement signal.

13. A method according to claim 1, wherein the deriving step includes deriving at least one second measurement signal being indicative of activity in the sympathetical branch of the autonomous nervous system of the patient.

14. A method according to claim 1, wherein the device is a display.

15. A method according to claim 1, wherein the device is a system for delivering drugs to the patient.

16. The method for monitoring subcortical responsiveness of a patient, the method comprising the steps of:
measuring at least two physiological signals from the patient using at least one sensor, the at least two physiological signals belonging to a group including an RRI signal, a plethysmographic signal, an EMG signal, a blood pressure signal, and a signal representing skin conductivity;
deriving at least two second measurement signals from the at least two physiological signals, the at least two second measurement signals being indicative of rain-related activity in the patient;
supplying a predetermined stimulus signal to the patient;
monitoring a response caused by the stimulus signal in the at least two second measurement signals, wherein the monitoring step is synchronized with the supply step;
determining, based upon a combination of the responses in the at least two second measurement signals monitored in the monitoring step, an indicator of subcortical responsiveness, the indicator being indicative of the patient's level of antinociception; and
outputting the indicator of subcortical responsiveness to a device.

17. A method according to claim 16, wherein
the monitoring step includes detecting changes caused by the stimulus signal in a plurality of second measurement signals; and
the determining step includes a step of calculating the indicator of subcortical responsiveness based on the changes detected in the plurality of second measurement signals.

18. A method according to claim 16, wherein the device is a display.

19. A method according to claim 16, wherein the device is a system for delivering drugs to the patient.

20. An apparatus for monitoring the subcortical responsiveness of a patient, the apparatus comprising:
first means for acquiring a plurality of first measurement signals from a patient, the first measurement signals being signals from a group including an RRI signal, a plethysmographic signal, an EMG signal, a blood pressure signal and a signal representing skin conductivity;
second means for deriving a plurality of second measurement signals from the first measurement signals, the second measurement signals being indicative of pain-related activity in the patient;
stimulator means for supplying a predetermined stimulus signal to the patient;
third means for monitoring a response caused by the stimulus signal in the second measurement signals, the third means being synchronized with the stimulator means; and
fourth means, responsive to the third means, for determining an indicator of subcortical responsiveness based upon the response caused in the plurality of second measurement signals, said indicator being indicative of the patient's level of antinociception.

21. An apparatus according to claim 20, further comprising means for synchronizing the stimulator means with a predetermined signal.

22. An apparatus according to claim 21, wherein the predetermined signal is indicative of a body function regulated by the autonomous nervous system of the patient.

23. An apparatus according to claim 20, wherein the stimulator means comprise control means for controlling the characteristics of the stimulus signal.

24. An apparatus according to claim 20, wherein the second means comprise filtering means for filtering the at least one first measurement signal.

* * * * *